United States Patent [19]
Thominet et al.

[11] Patent Number: 4,594,428
[45] Date of Patent: Jun. 10, 1986

[54] NOVEL SUBSTITUTED HETEROCYCLIC AMINES AND METHODS OF PREPARATION THEREOF

[75] Inventors: Michel L. Thominet, Paris; Jacqueline F. Franceschini, L'Hay les Roses, both of France

[73] Assignee: Societe d'Etudes Scientifiques et Industrielles de L'ile-de-France, Paris, France

[21] Appl. No.: 456,523

[22] Filed: Jan. 7, 1983

Related U.S. Application Data

[62] Division of Ser. No. 162,796, Jun. 25, 1980, Pat. No. 4,379,161.

[51] Int. Cl.⁴ .................. C07D 207/08; C07D 207/04
[52] U.S. Cl. ...................................... 548/570; 548/400
[58] Field of Search ...................... 548/413, 570, 400

[56] References Cited

U.S. PATENT DOCUMENTS 2,826,588  3/1958  Feldkamp et al. ............... 548/570
3,109,845  11/1963 Seeger et al. ..................... 548/400
3,117,976  1/1964  Meuta et al. ...................... 548/570
3,172,912  3/1965  Easton et al. ..................... 548/400
3,192,230  6/1965  Lunsford et al. ................. 548/400
3,202,675  8/1965  Albertson ......................... 548/570

FOREIGN PATENT DOCUMENTS 7120568  7/1980  Japan ................................ 548/570

OTHER PUBLICATIONS

"Pyrrolidines. IV. The Investigation of the Synthesis of 1-Methyl-2-pyrrolidineethanol" by H. Wu.

Primary Examiner—Glennon H. Hollrah
Assistant Examiner—Dara Dinner
Attorney, Agent, or Firm—Arnold, White & Durkee

[57] ABSTRACT

The present invention concerns compound useful as intermediates in the preparation of heterocyclic phenoxy amines of the formula

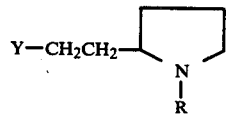

wherein Y is hydroxyl or chlorine and R is 1-cyclohexenylmethyl.

3 Claims, No Drawings

NOVEL SUBSTITUTED HETEROCYCLIC AMINES AND METHODS OF PREPARATION THEREOF

This is a division of application Ser. No. 162,796, filed June 25, 1980, now U.S. Pat. No. 4,379,161.

The present invention concerns a novel substituted heterocyclic phenoxyamines having the general formula I, their salts of addition with pharmaceutically acceptable acids, their quaternary ammonium salts, their N-oxides and the methods of preparing such compounds, and the medicaments which contain same as active principles:

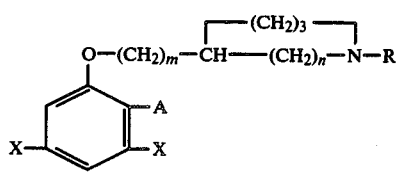

(I)

In the above formula:
m=0 or 2
n=0 or 2
provided that m+n=2
and in which:
A is hydrogen,
  alkoxy with 1-4 C-atoms in the alkyl group, such as methoxy, ethoxy, linear or ramified propoxy, butoxy,
  alkenyloxy with 2-6 C-atoms in the alkenyl group, such as vinyloxy, propenyloxy (allyl), butenyloxy, pentenyloxy, hexenyloxy,
X=halogen, such as F, Cl, Br.
R=H, lower alkyl with 1-6 C-atoms such as methyl, ethyl, linear or ramified propyl, butyl, pentyl or hexyl
  cycloalkyl with 3 or more than 3 C-atoms such as cyclopropyl, cyclobutyl, cyclopentyl, cyclohexyl, methylcyclobutyl, methylcyclopentyl, methylcyclohexyl, ethylcyclohexyl.
  alkenyl with 2-6 C-atoms such as vinyl, propenyl (2) (allyl), butenyl, pentenyl, hexenyl
  cycloalkenyl expecially with more than 3 C-atoms such as cyclobutenyl, cyclopentenyl, cyclohexenyl, methylcyclobutenyl, methylcyclopentenyl, methylcyclohexenyl, ethylcyclohexenyl,
  cycloalkyl or cycloalkenyl lower alkyl, whereby the cycloalkyl, cycloalkenyl and lower alkyl groups are defined as above, such as cyclopropylmethyl, cyclopropylethyl, cyclobutylmethyl, cyclobutylethyl, cyclopentylmethyl, cyclopentylethyl, cyclopentenylmethyl, cyclopentenylethyl, cyclohexylmethyl, cyclohexylethyl, cyclohexenylmethyl, cyclohexenylethyl.

The compounds of the invention according to a first embodiment can be illustrated by the following general formulas II and III whereby compounds according to formula III are the most preferred ones:

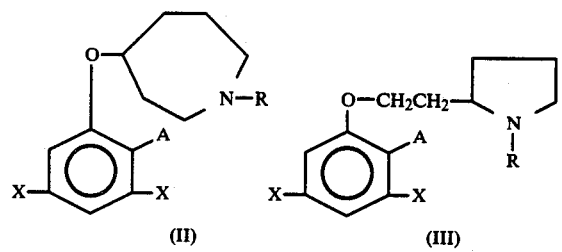

with R, A and X as defined above.

Especially preferred are compounds according to the following formula (IV)

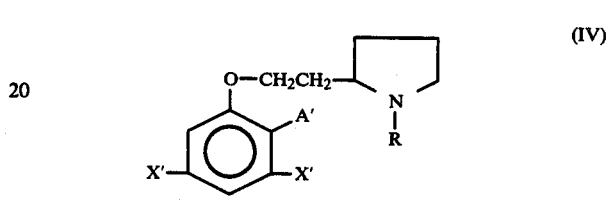

in which
A' represents H, OMe, OEt
X' represents Cl or Br
R is defined as above.

By virtue of the presence of an asymmetric carbon in such compounds, they may occur in racemic form or in an optically active form after resolution.

The products of the invention present interesting pharmacological properties in regard to the central nervous system, in particular as local anaesthetics.

The invention therefore extends to the use as a medicament of the compounds of general formula I.

The invention also concerns the pharmaceutical compositions which, as the active principle, contain at least one of the compounds of general formula I, associated with a pharmaceutical inert excipient.

The invention also concerns a process for producing the compounds of general formula I, characterised in that a phenol corresponding to general formula V:

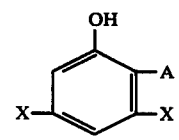

wherein A and X are as defined above, is condensed with a compound of general formula VI:

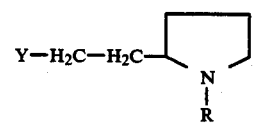

wherein R is as defined above and Y is an anionic residue which is capable of being eliminated, the residue Y will be for example a halogen atom, in particular chlorine, bromine or iodine, to produce a compound of general formula I:

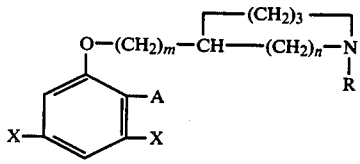

wherein the definitions of m, n, A, X and R remain unchanged.

These compounds can be salified. They can be resolved by reaction with an optically active acid into their pharmacologically active optical isomers.

The phenols of formula V are used in the form of phenolates of alkali metals, in particular sodium phenolate, which is produced for example by reaction of the phenols with the alcoholates of alkali metals.

The reaction between the compounds of formula V and the compounds of formula VI is carried out in an inert organic solvent such as toluene, xylene .... Operation is effected at the reflux temperature of the reaction mixture.

Compounds are produced which are then separated, isolated and purified in accordance with normal methods, for example extraction, formation of salts, recrystallization, chromatrography, etc.

Salification of the compounds of formula I is preferably effected by the addition of a mineral acid such as hydrochloric acid, hydrobromic acid, phosphoric acid or an organic acid such as fumaric acid, citric acid or oxalic acid.

The compounds of general formula I can also react for example with alkyl sulphates or halides to give quaternary ammonium salts.

The compounds of formula I can be oxidised in per se known manner for example by means of hydrogen peroxide and manganese dioxide to give the corresponding N-oxides.

Resolution of the compounds of general formula I is effected with an optically active acid.

The starting compounds of formula V wherein X represents chlorine can be prepared from phenols by acetylation, chlorination, de-acetylation and then purification.

The starting compounds of formula V wherein X represents bromine can be prepared from o-nitrophenol by bromination, alkylation of the phenol function, reduction of the nitro group, diazotization and decomposition.

The starting compounds of formula VI can be prepared in accordance with the fourth method described by YAO-HUA-WU and J R CORRIGAN, J ORG CHEM (1961) page 1531.

In order to illustrate the technical features of the present invention, a number of embodiments will be described hereinafter, it being appreciated that these embodiments are not limiting in regard to their manner of performance and the uses to which they can be put.

EXAMPLE I 1-methyl-4-[2-methoxy-3,5-dichlorophenoxy]hexamethylene imine 1-methyl-2-[2-methoxy-3,5-dichlorophenoxyethyl]pyrrolidine 13 g of sodium is dissolved in 180 ml of ethanol in a 2 liter balloon flask provided with a sealed agitator, a reflux condenser and a thermometer, and 108 g of 3,5 dichloroguaiacol (0.56 mole) and 300 ml of dry toluene is added to the resulting solution.

The condenser is then replaced by a 40 cm Vigreux column and the whole of the alcohol is removed by azeotropic distillation. As the alcohol is removed, the sodium salt of 3,5-dichloroguaiacol crystallizes in a thick mass.

At the end of the distillation step, a volume of toluene equal to that which was carried over is added, and then cooling is effected.

The Vigreux column is again replaced by the reflux condenser and 103 g of 1-methyl-2-[2-chloroethyl] pyrrolidine (0.56 mole+25% excess) is added. The resulting mixture is put under gentle reflux. The mixture rapidly fluidifies with heat clearly being given off.

As soon as the reaction has calmed, the mixture is again heated under reflux and reflux heating is maintained for 8 hours.

The reaction mixture is then cooled and dissolved with 400 ml of water and 80 ml of concentrated hydrochloric acid. The toluene is decanted and washed twice with acid water.

The aqueous solutions are combined, filtered with black and rendered alkaline by the addition of 20% ammonia until the phenolphthaleine changes colour. The oil which separates out is decanted and extracted with ether. The ethereal solution is dried over potassium carbonate.

The ether is then distilled, concluding under vacuum, until constant weight is attained.

182 g of product (theory: 170 g) is obtained.

According to T.L.C. analysis [silica MERCK 5554, eluent=benzene, ethanol, ammonia (84:15:1)], the product obtained is a mixture in substantially equal parts of two isomers: 1-methyl-4-[2-methoxy-3,5-dichlorophenoxy] hexamethylene imine and 1-methyl-2-[2-methoxy-3,5-dichlorophenoxyethyl]pyrrolidine.

The mixture of bases is dissolved in 400 ml of methyl ethyl ketone and 20.5 g of dry hydrochloric acid (0.56 mole) in solution in 40 ml of methyl ethyl ketone is added.

Crystallisation is begun, and is left overnight. The hydrochloride is then drained, washed with methyl ethyl ketone and dried at 40° C.

97 g of product is obtained: melting point: 155°-7° C.

According to T.L.C. analysis, the major part of this hydrochloride comprises hexamethylene imine derivative.

The mother liquirs are subjected to further treatment to produce the pyrrolidine derivative.

The hydrochloride is recrystallized twice in 185 and 150 ml of acetonitrile respectively. 69.5 g of 1-methyl-4-[2-methoxy-3,5-dichlorophenoxy]hexamethylene imine hydrochloride is collected, with a melting point of 161° to 162.5° C.

The mother liquors of the hydrochloride are dissolved with a little water and the methyl ethyl ketone is distilled. The remaining solution is diluted with 325 ml of water, filtered with black and rendered alkaline by the addition of 20% ammonia until the phenolphthaleine turns colour. The oil which separates off is decanted and extracted with ether. The ethereal solution is dried over potassium carbonate and then the ether is distilled, concluding under vacuum, until constant weight is reached. Weight obtained: 82 g.

By hot dissolution in 230 ml of isopropanol of the 82 g of base (0.27 mole) and 31.5 g of fumaric acid (0.27 mole), followed by cooling and filtration of the precipitate formed, 109.5 g of fumarate is obtained.

This is recrystallized from 275 ml of methanol. 78 g of 1-methyl-2-[2-methoxy-3,5-dichlorophenoxyethyl] pyrrolidine fumarate with a melting point of 179° to 180° C. is obtained.

T.L.C. analysis reveals the presence of a small amount of hexamethylene imino derivative which is not detected by the NMR spectrum.

EXAMPLE II

Dextrorotatory 1-methyl-2-[2-methoxy-3,5-dichlorophenoxyethyl]pyrrolidine

The fumarate of the racemic product is converted into base form by being rendered alkaline with aqueous ammonia and extraction with ether. 161 g of this base (0.53 mole) is dissolved in 320 ml of methanol and a solution of 199 g of L (+)dibenzoyltartaric acid (0.53 mole) in 400 ml of methanol is added. The dibenzoyltartrate crystallizes immediately. After being left overnight, it is drained, washed with 300 ml of methanol and dried at 40° C. 161 g of product with a melting point of 160° is obtained:

$[a]D^{20} = -37°$ (5% dimethylformamide solution), 157 g of debenzoyltartrate is dissolved in 200 ml of dimethylformamide and then 65 ml of water is added (which gives 80% dimethylformamide).

After cooling, the salt which recrystallizes is drained, washed with 200 ml of 80% dimethylformamide and then with water, and dried at 40°. 136 g of product is collected: melting point: 140°-1° C.; $[a]D^{20} = -36.5°$ (5% dimethylformamide solution).

136 g of dibenzoyltartrate, 600 ml of water, 45 ml of 20% ammonia and 300 ml of ether are introduced into a 3 liter balloon flask provided with an agitator. The base which precipitates is immediately dissolved in the ether. It is decanted. The aqueous solution is extracted with ether and the resulting etherial solution is dried on potassium carbonate and then the ether is distilled, concluding under vacuum until a constant weight of 61.5 g is reached.

$[a]D^{20} = 47.5°$ (5% dimethylformamide solution).

The 61.5 g of base (0.202 mole) is heated in the presence of 170 ml of water and 23.5 g of fumaric acid (0.202 mole) until dissolution occurs. The boiling solution produced is filtered with black. By cooling, the fumarate crystallizes slowly. It is drained, washed with water and dried at 40° C. 74 g of fumarate with a melting point of 157° to 157.5° C. is obtained. $[a]D^{20} = +19.5°$ (5% dimethylformamide solution).

EXAMPLE III

Levorotatory 1-methyl-2-[2-methoxy-3,5-dichlorophenoxyethyl]pyrrolidine

The alcoholic liquors resulting from the preparation of dextrorotatory 1-methyl-2-[2-methoxy-3,5-dichlorophenoxy-ethyl]pyrrolidine dibenzoyltartrate and containing about 88 g of base are concentrated. The residue is dissolved with 400 ml of water, 60 ml of 20% ammonia and ether, with vigorous stirring. The base which precipitates is dissolved in ether. The ethereal solution is decanted. The aqueous phase is extracted three times with ether.

The ethereal phases are combined and dried on K₂CO₃. The ether is distilled, concluding under vacuum, until a constant weight is attained. 69.5 g of base is produced.

67 g of the base (0.22 mole) is dissolved in 140 ml of methanol and then a solution of 83 g of D(−)dibenzoyltartric acid (0.22 mole) in 165 ml of methanol is added. The dibenzoyltartrate crystallizes immediately. It is drained, washed with methanol and dried at 40° C. Weight produced: 126 g. Melting point: 133°-4° C. $[a]D^{20} = +37.2°$ (5% dimethylformamide solution).

124 g of debenzoyltartrate is dissolved in water and an excess of ammonia. The base which is separated is immediately extracted with ether.

The ethereal solution is decanted and the aqueous phase is extracted with ether. The ethereal phases are combined and dried on potassium carbonate.

The ether is then distilled, concluding under vacuum, until constant weight is obtained: 56 g. $[a]D^{20} = -44.8°$ 54 g of base (0.178 mole), 145 ml of water and 21 g of fumaric acid (0.178 mole) are introduced into a 500 ml balloon flask provided with a reflux condenser, and the mixture is heated until dissolution occurs. The boiling solution obtained is filtered with black. Cooling causes the fumarate to crystallise. It is drained, washed with water and dried at 40°.

68 g of product is obtained, with a melting point of 157°-8° C. $[a]D^{20} = -17.8°$ (5% dimethylformamide solution).

EXAMPLE IV 1-allyl-4-[2-methoxy 3,5-dichlorophenoxy]hexamethylene imine 1-allyl-2-[2-methoxy 3,5-dichlorophenoxyethyl]pyrrolidine Following the mode of operation of the reaction of 3,5-dichloroguaiacol with 1-methyl-2-[2-chloroethyl]-pyrrolidine, using 246 g of 3,5-dichloroguaiacol (1.275 mole) and 221 g of 1-allyl-2-[2-chloroethyl]pyrrolidine (1.275 mole), the result obtained is 411 g of a mixture of substantially equal parts of 2 isomers: 1-allyl-4-[2-methoxy 3,5-dichlorophenoxy]hexamethylene imine and 1-allyl-2-[2-methoxy 3,5-dichlorophenoxyethyl]-pyrrolidine.

397 g of the mixture of bases (1.20 mole) is dissolved in 1250 ml of acetonitrile and then 230 g of dry citric acid (1.20 mole) is added. The suspension is heated until total dissolution occurs, then the solution is chilled overnight. The precipitate is drained, washed with 1200 ml of acetonitrile, dried in air and then in a drying oven at 40° C. 538 g of a mixture of citrates of the two products is obtained. This mixture is recrystallized three times, being passed over in 95° alcohol. 227 g of product is obtained, whose NMR spectrum is compatible with the hexamethylene imine structure: melting point 90°-5° C.

The acetonitrile and the alcohol recrystallization liquors are distilled, concluding under vacuum. The residue is dissolved with water and filtered with black. The base is then precipitated by the addition of 20% ammonia until the phenolphthaleine turns colour. The oil which separates off is decanted and extracet with ether. The ethereal solution is dried over potassium carbonate and the ether is distilled, concluding under vacuum, until constant weight is attained. 184 g of base (0.56 mole) is produced, which is dissolved in the hot state in 550 ml of isopropanol and 65 g of fumaric acid (0.56 mole). Cooling causes the fumarate to crystallise, and it is drained, washed with isopropanol, dried in air and then at a temperature of 40° C. 141 g of product with a melting point of 135°-6° C. is produced.

140 g of fumarate is recrystallized from 275 ml and then 145 ml of isopropanol and finally 190 ml of water. 90 g of 1-allyl-2-[2-methoxy, 3,5-dichlorophenoxyethyl]-pyrrolidine fumarate is obtained: melting point: 137°-8° C.

EXAMPLE V 1-ethyl-2-[3,5-dichlorophenoxyethyl]pyrrolidine 19 g of sodium is dissolved in 245 ml of absolute alcohol in a 2 liter balloon flask provided with a sealed agitator, a reflux condenser and a thermometer. The ethylate solution is cooled, and 133 g of dichlorophenol (0.815 mole) and 430 ml of dry toluene is added thereto. The reflux condenser is replaced by a Vigreux column and the alcohol is removed by azeotropic distillation. The sodium salt of the dichlorophenol precipitates and thickens the medium which however remains stirrable.

After cooling, the Vigreux column is replaced by a reflux condenser, 139 g of 1-ethyl-2-[B-chloroethyl]pyrrolidine was prepared from its hydrochloride immediately before use thereof.

When the reaction is concluded, the reaction mixture is dissolved with 1.8 liters of water and 85 ml of concentrated hydrochloric acid. The toluene phase is decanted and then washed with 100 ml of water and 10 ml of concentrated hydrochloric acid.

The aqueous phases are combined, filtered with black and rendered alkaline by the addition of 20% ammonia until the phenolphthaleine turns colour. The oil which is separated off is extracted with ether and the ethereal solution is dried on potassium carbonate. After the removal of ether, the product is distilled under vacuum.

Middle fraction: 180°-2° C. under a pressure of 5 mmHg. Weight: 175 g.

The 175 g of base (0.61 mole) is dissolved in 335 ml of methylethylketone and then a solution of 22.5 g of dry hydrochloric acid (0.61 mole) in 260 ml of methyl ethyl ketone is added, until the methyl red turns. The hydrochloride slowly crystallizes and is drained, washed with 130 ml of methyl ethyl ketone and dried in a drying oven. 151.5 g of hydrochloride is produced.

Chromatographic analysis of this substance (silica Merck 5554-eluent: benzene-ethanol-ammonia 84:15:1) shows that it is a mixture of hydrochlorides of 1-ethyl-2-[3,5-dichlorophenoxyethyl]pyrrolidine and 1-ethyl-4-[3,5-dichlorophenoxy]hexamethylene imine. The mixture has a higher pyrrolidine content.

150 g of the hydrochlorides mixture is recrystallized from 150 ml and then 225 ml of acetronitrile. 46 g of substance with a melting point of 138°-140° C. is collected. This is then recrystallized from 95 ml and then 50 ml of isopropanol, giving 27 g of product with a melting point of 152°-3° C. Chromatographic analysis has only a single spot.

EXAMPLE VI 1-methyl-2-[2-methoxy-3,5-dibromophenoxyethyl]pyrrolidine 3,5-Dibromo quaiacol (a) Diazotization:

725 ml of concentrated sulphuric acid is introduced into a 3 liter balloon flask provided with an agitator, a thermometer and a dropping funnel and 177 g of 3,5-dibromoo.anisidine (0.63 mole) is added gradually. The temperature rises to 40° C. The resulting solution is cooled and then a solution of 52.5 g of sodium nitrite (0.63 mole+20% excess) in 80 ml of water is poured in dropwise at a temperature of from 0° to +5° C.

When the diazotization operation is concluded, the mixture is agitated by a further 2 hours at from 0° to +5° C. and then the solution is poured over 1200 g of ice: a suspension is produced.

(b) Decomposition:

120 g of copper sulphate is dissolved in 1400 ml of water in a Vigreux balloon flask, and raised to boiling, and the diazo compound is added dropwise. It is decomposed and the phenol formed is subjected to vapour distillation. When the introduction operation is concluded, the distillation operation is continued. 12 liters of water is distilled. The water is decanted and the aqueous solution is extracted with ether.

The organic phase is dissolved with dilute sodium hydroxide.

Decantation is effected, followed by acidification of the aqueous phase with hydrochloric acid. The phenol reprecipitates. It is extracted with ether and the ethereal solution is dried over $Na_2SO_4$, the ether then being distilled, concluding under vacuum, until a constant weight is attained. The residue is dissolved with two volumes of petroleum ether. The phenol dissolves and then crystallizes upon cooling. It is drained, washed with petroleum ether and dried in air. Weight: 54 g. Melting point: 59°-60° C. After crystallization from petroleum ether, the resulting produce is 43 g of 3,5-dibromoquaicol with a melting point of 63°-4° C.

1-Methyl-2-[2-methoxy-3,5-dibromophenoxyethyl]-pyrrolidine.

15 g of sodium is dissolved in 215 ml of absolute ethanol in a 2 liter balloon flaks provided with an agitator, a reflux condenser and a thermometer. 187 g of dibromoguaiacol (0.66 mole) in 365 ml of dry toluene is added. The whole of the alcohol is removed by azeotropic distillation. The result is a very thick suspension to which 190 ml of toluene is added. Cooling is effected, followed by the addition of 102.5 g of 1-methyl-2-[B-chloroethyl]pyrrolidine (0.66 mole+5% excess). This is heated for 8 hours under reflux.

The reaction mixture is then dissolved with 500 ml of water and 66 ml of hydrochloric acid (d=1.18).

The toluene layer is decanted and washed with 200 ml of 1/20 dilute hydrochloric acid.

The aqueous solutions are combined together and filtered with black and then rendered alkaline with 20% ammonia.

The oil which decants is extracted with ether.

The ethereal solution is dried on $K_2CO_3$ and then the ether is distilled until a constant weight is attained. 165 g of base is produced, which, according to C.C.M. analysis, is a mixture of the following isomers: 1-methyl-4-[2-methoxy-3,5-dibromophenoxy]hexamethylene imine and 1-methyl-2-[2-methoxy-3,5-dibromophenoxyethyl)pyrrolidine.

164 g of base (0.448 mole) is dissolved in ethanol and a solution of 52 g of fumaric acid (0.448 mole) in 685 ml of absolute alcohol is added. Cooling causes the fumarate to crystallize and it is then drained, washed with alcohol and dried. T.L.C. analysis of this substance indicates an enrichment in respect of pyrrolidinic derivative. The fumarate is purified by recrystallization from 320 ml of methanol, followed by 2 recrystallization steps from 100 ml and 80 ml of dimethylformamide respectively. 33 g of 1-methyl-2-[2-methoxy-3,5- dibromophenoxyethyl]-pyrrolidine fumarate with a melting point of 192° C. is produced.

EXAMPLE VII 1-ethyl-2-[2-methoxy-3,5-dichlorophenoxyethyl]pyrrolidine

Using the mode of operation of the preceding Examples, the reaction of 333 g of quaiacol (1.72 mole) and 292 g of 1-ethyl-2-[B-chloroethyl]pyrrolidine (1.72 mole+5% excess) which is prepared extemporaneously from its hydrochloride results, after distillationm, in 414 g of product which distills at 173°–180° C. under a pressure of 1 mm Hg. This substance is dissolved in 800 ml of methyl ethyl ketone. A solution of 47.5 g of dry hydrochloric acid in 400 ml of methyl ethyl ketone is added. The hydrochloride which crystallizes is cooled and then drained, washed with methyl ethyl ketone and dried in a drying oven at 40° C. The result is 306.5 g of hydrochloride with a melting point of 126°–8° C., which is recrystallized from 613 ml of acetone.

252 g of 1-ethyl-2-[2-methoxy-3,5-dichlorophenoxyethyl]pyrrolidine hydrochloride is collected: melting point: 129°–130° C.

EXAMPLE VIII

Dextrorotatory 1-ethyl-2-[2-methoxy-3,5-dichlorophenoxyethyl]pyrrolidine 175 g of 1-ethyl-2-[2-methoxy-3,5-dichlorophenoxyethyl]pyrrolidine (0.55 moles) is dissolved in 260 ml. of 95° ethanol. A solution of 82.5 g of dextrorotatory tartaric acid (0.55 mole) in 260 ml. of 95° ethanol is added. After cooling and seeding, the tartrate crystallizes. It is drained, washed with 100 ml of 95° ethanol and dried at a temperature of 40° C. 104 g of dextrorotatory tartrate is produced: $[a]D^{20} = +21.5°$ (5% aqueous solution.

103.5 g of tartrate is recrystallized from 207 ml of 95° ethanol. 82 g of product is obtained: $[a]D^{20} = +24.3°$ (5% aqueous solution).

81 g of tartrate is dissolved in 425 ml of luke-warm water and then the base is precipitated by the addition of 20% ammonia. The oil which decants is extracted with ether. After drying of the ethereal phase and evaporation, 47.5 g of base is obtained. $[a]D^{20} = +55.8°$ (5% dimethylformamide solution).

46 g of base (0.145 mole) is dissolved in 140 ml of ethyl acetate and a solution of 5.5 g of dry hydrochloric acid (0.145 mole) in 55 ml of ethyl acetate is added.

The hydrochloride which crystallizes is drained, washed with ethyl acetate and dried in a drying oven at 40° C.

47.5 g of product with a melting point of 121°–2° C. is produced. $[a]D^{20} = +18.9°$ (5% aqueous solution).

EXAMPLE IX

Levorotatory 1-ethyl-2-[2-methoxy-3,5-dichlorophenoxyethyl]pyrrolidone

The alcoholic liquors originating on the one hand from precipitation and on the other hand from recrystallization of the dextrorotatory tartrate of 1-ethyl-2-[2-methoxy-3,5-dichlorophenoxyethyl]pyrrolidine is dissolved with 850 ml of water and concentrated down to a volume of 400 ml.

A solution of 31 g of potassium chloride (0.375 mole+10% excess) in 140 ml of water is added. The potassium tartrate which precipitates is drained and washed with water.

The liquors are rendered alkaline with 20% ammonia. The oil which separates is extracted with ether, and the ethereal solution is dried on potassium carbonate. The ether is then distilled, terminating under vacuum, until a constant weight is obtained. 107 g of product is obtained, being a mixture of approximately 20% dextrorotatory base and 80% levorotatory base.

This product is dissolved in 160 ml of absolute ethanol and then 53 g of levorotatory tartaric acid dissolved in the hot state in 160 ml of ethanol is added. The solution is filtered and then cooled. The tartrate which crystallizes is drained, washed with 95° ethanol and dried in a drying oven at 40° C. Weight obtained: 107.5 g $[a]D^{20} = -21.6°$ (5% aqueous solution).

The tartrate is recrystallized from 215 ml of 95° ethanol. 95 g of substance is collected, which has a melting point of about 80° to 85° C., then being recrystallized and having a melting point of 102°–3° C. It contains 1 mole of water. $[a]D^{20} = -24.7°$ (5% aqueous solution).

94 g of tartrate is dissolved is luke-warm water. The base is precipitated by the addition of 20% ammonia and then extracted with ether. 52.5 g of base is obtained:

$[a]D^{20} = -57.5°$ (5% dimethylformamide solution).

51 g of base (0.16 mole) is dissolved in 150 ml of ethyl acetate. A solution of 5.9 g of dry hydrochloric acid in 65 ml of ethyl acetate is added. The hydrochloride crystallizes and is drained, washed with ethyl acetate and dried in a drying oven at 40° C. The resulting product is 41.5 g of a substance with a melting point of 117°–119° C.: $[a]D^{20} = -20.4°$ (5% aqueous solution).

EXAMPLE X 1-ethyl-2-[2-ethoxy-3,5-dichlorophenoxyethyl]pyrrolidine

2-Ethoxy 3,5-dichlorophenol.

152 g of 2-ethoxy phenol (1.15 mole), 136 g of acetic anhydride and 10 drops of concentrated sulphuric acid are introduced into a balloon flask provided with a reflux condenser. The reaction is highly exothermic and the temperature rises towards 80° C. When the reaction is calmed, the mixture is heated on a water bath for 15 minutes. The sulphuric acid is neutralised by the addition of sodium acetate.

345 ml of acetic acid and, in portions, with the temperature being kept at from 20° to 25° C., 271 g of 1,3-dichloro 5,5-dimethylhydantoin (1.15 mole+20% excess) are added. The suspension is heated at 50° to 55° C. for 97 hours. All the hydantoin is very rapidly dissolved.

The solution is poured into 4 liters of water. The chlorinated derivative, which is liquid, is decanted and then deacetylated immediately by heating under reflux, in the presence of dilute caustic soda solution, until total dissolution occurs. The solution is diluted with water and the phenol is precipitated by the addition of concentrated hydrochloric acid. It is decanted. The aqueous phase is extracted with ether and the ethereal phase is dried on sodium sulphate. After elimination of the ether, 2-ethoxy, 3-5-dichlorophenol is distilled under vacuum. 166 g of product is collected, which distills at a temperature of 130°–4° C. under a pressure of 15 mmHg. The product crystallizes. Melting point: 45° C.

1-Ethyl-2-[2-ethoxy-3,5-dichlorophenoxyethyl]pyrrolidine.

A solution of sodium ethylate is prepared from 9.2 g of sodium and 120 ml of absolute ethanol and then 83 g of 2-ethoxy 3,5-dichlorophenol (0.4 mole) is added. The alcohol is distilled and then 240 ml of dry xylene is added. The last traces of alcohol are removed by azeotropic distillation. After cooling, 71 g of 1-ethyl-2-[B-chloroethyl]pyrrolidine (0.4 mole+10% excess) is added and the reaction mixture is left overnight.

The mixture is heated under reflux for four hours and then cooled and dissolved with 600 ml of water and 30 ml of concentrated hydrochloric acid.

The aqueous phase is decanted and filtered with black and then the base is precipitated by the addition of 60 ml of concentrated ammonia. It is then decanted. The aqueous solution is extracted with methylene chloride and the organic phase is dried on potassium carbonate. After elimination of the solvent, the residual product is distilled under vacuum. 101 g of base is produced. Boiling point: 198°-200° C. at 8 mmHg.

The base is dissolved in 300 ml of absolute ethanol. A solution of 58.5 g of anhydrous citric acid in 200 ml of ethanol is added. The citrate formed is drained, washed with alcohol and dried in the air. Melting point: 95°-100° C.

It is recrystallized, being passed over black, from 130 ml of ethanol. 124 g of 1-ethyl-2-[2-ethoxy-3,5-dichlorophenoxyethyl]pyrrolidine citrate is produced: melting point: 95°-100° C.

EXAMPLE XI 1-cyclohexyl 4-[2-methoxy 3,5-dichlorophenoxy]hexamethylene imine 1-cyclohexyl 2-[2-methoxy 3,5-dichlorophenoxyethyl]pyrrolidine Using the process of Example 1, the reaction of 116 g of 3,5-dichloroguaiacol (0.6 mole) and 148 g of 1-cyclohexyl 2-[2-chloroethyl]pyrrolidine (0.6 mole+11%) results in 233 g of product (theory: 222 g) which, according to T.L.C. analysis, is a mixture of 2 isomers:

1-cyclohexyl 4-[2-methoxy 3,5-dichlorophenoxy]hexamethylene imine.

1-cyclohexyl 2-[2-methoxy 3,5-dichlorophenoxyethyl]pyrrolidine.

233 g of base is dissolved in 450 c. of water and 53 cc of concentrated hydrochloric acid. The solution is cooled, with seeding to start crystallization, and the mixture is left overnight. 163 g of hydrochloride is produced. The hydrochloride contains virtually only hexamethylene imino derivative.

The hydrochloride is recrystallized with filtration on black, producing 150 g of 1-cyclohexyl 4-[2-methoxy-3,5-dichlorophenoxy]hexamethylene imine hydrochloride with a melting point of 174°-176° C.

The aqueous liquors are then filtered with black and rendered alkaline by the addition of 20% ammonia. The oil which decants is extracted with ether. The ethereal solution produced is dried on potassium carbonate and then the ether is distilled, concluding under vacuum, until constant weight is attained. Weight produced: 92 g.

86 g of base (0.23 mole) is dissolved in 260 ml of acetonitrile and 53 g of phosphoric acid (2×0.23 mole). The phosphate which is formed precipitates in the form of an oil which seems to be crystallized after being at rest overnight. This phosphate is drained, washed with acetonitrile, dried in air and then under vacuum on sulphuric acid, but the product obtained is half crystallized. It is dissolved in 150 ml of absolute ethanol and left overnight. It is then properly crystallized. It is drained, washed with ethanol and dried at a temperature of 40° C. 55 g of 1-cyclohexyl 2-[2-methoxy-3,5-dichlorophenoxy ethyl]pyrrolidine bis-phosphate with a melting point of 138°-138.5° C. is produced.

EXAMPLE XII 1-cyclopropylmethyl-4-[2-methoxy-3,5-dichlorophenoxy]hexamethylene imine 1-cyclopropylmethyl-2-[2-methoxy-3,5-dichlorophenoxyethyl]pyrrolidine (a) 1-cyclopropylmethyl-2-[2-chloroethyl]pyrrolidine hydrochloride.

(1) 1-cyclopropylmethyl-2-carbethoxy methyl-5-pyrrolidone.

78 g of cyclopropylmethylamine (1.1 mole) and 220 g of 3-hexenedioic acid diethyl ester are introduced into a liter autoclave. The mixture is heated to 165° C. and then kept at that temperature for 8 hours. After cooling, the product is distilled under vacuum, first eliminating the alcohol, then obtaining 155 g of a compound which distills at 157°-160° C. under 3 mm of Hg.

(2) 1-cyclopropylmethyl 2-(2-hydroxyethyl)pyrrolidine.

52.5 g of lithium aluminum hydride (2×0, 69 mole) and 390 ml of dry tetrahydrofuran are introduced into a 3 liter balloon flask provided with a stirrer, a reflux condenser and a dropping funnel. 155 g of a solution of 1-cyclopropylmethyl 2-carbethoxymethyl 5-pyrrolidone is then dropped into the suspension in 2 hours. The reflux is then kept for three hours and a half.

After cooling, the lithium aluminum hydride in excess is eliminated by slow addition of 75 ml of water while providing outside cooling.

The suspension is treated with 1050 ml of 6 N hydrochloric acid, then with 580 g of seignette salt and 580 ml of water. After addition of 470 ml of 30% soda lye, the organic phase is decanted off and dried on potassium carbonate. The tetrahydrofuran is evaporated, then 1-cyclopropyl methyl-2-[2-hydroxyethyl]pyrrolidine is distilled under vacuum.

102 g (yield=87.5%) of a compound which distills at 125°-127° C. under 10 mm of Hg is obtained.

(3) 1-cyclopropylmethyl 2-[2-chloroethyl]pyrrolidine hydrochloride.

172 g of 1-cyclopropylmethyl 2-[2-hydroxyethyl]pyrrolidine (1.02 mole) and 510 ml of chloroform are introduced into a 3 liter balloon flask provided with a stirrer, a reflux condenser, a thermometer and a dropping funnel. The solution is cooled to 10° C. then 151.5 g of thionylchloride (1.02 mole+25%) is dropped in while keeping the temperature between 10° and 15° C.

The mixture is then heated under reflux for 7 hours.

The chloroform is distilled under vacuuum until constant weight—254 g of hydrochloride in a liquid state is obtained.

After dissolution in water, treatment with soda and extraction with ether, 175 g of amine is obtained (yield=92%).

(b) 1-cyclopropylmethyl 4-[2-methoxy-3,5-dichlorophenoxy]hexamethylene imine.

1-cyclopropylmethyl2-[2-methoxy-3,5-dichlorophenoxyethyl]pyrrolidine.

Using the process of Example 1 as described above, the reaction of 174 g of 3,5-dichloroguaiacol (0.90 mole)

and 186 g of 1-cyclopropylmethyl-2-[2-chloroethyl]pyrrolidine (0.90 mole+10%) results in 329 g of product (theory: 310 g) which, according to T.L.C. analysis, is a mixture of 2 isomers:

1 cyclopropylmethyl-4-[2-methoxy-3,5-dichlorophenoxy]hexamethylene imine, and 1-cyclopropylmethyl-2-[2-methoxy-3,5-dichlorophenoxyethyl]pyrrolidine.

328.5 g of base is dissolved in 500 ml of ethanol and 173 g of citric acid (0.9 mole) dissolved in 1000 ml of ethanol is added to the resulting solution. The citrate crystallizes slowly. It is drained, washed with 300 ml of ethanol and dried at 40° C. 389 g of citrate with a melting point of 60° to 65° C. is produced which has a greater content of hexamethylene imino derivative than pyrrolidine derivative.

This citrate is recrystallized with filtration on black successively from 780 ml of acetonitrile, 510 ml and then 645 ml of methyl ethyl ketone. 189 g of 1-cyclopropylmethyl-4-[2-methoxy-3,5-dichlorophenoxy]hexamethylene imine with a melting point of 71°–73+ C. and which does not have more than 1 spot in the T.L.C. analysis is produced. The alcoholic liquors from crystallization of the citrate are concentrated down to a volume of 280 ml. They are diluted with a liter of water and the solution is rendered alkaline by the addition of 20% ammonia. The oil which decants is extracted with methylene chloride. The organic phase is dried on potassium carbonate and then methylene chloride is distilled, concluding under vacuum, until a constant weight is attained. Weight produced: 76 g.

69 g of base (0.2 mole) is dissolved in 275 ml of absolute ethanol. 23 g of fumaric acid (0.2 mole) is added, and the mixture is heated until dissolution occurs. This is followed by cooling. The fumarate which crystallizes is drained, washed with 60 ml of ethanol and dried in a drying oven. Weight produced: 65 g.

This product is a mixture containing a majority proportion of pyrrolidino derivative. It is recrystallized with filtration with black from 130 ml of 95° ethanol.

The resulting product is 45 g of 1-cyclopropylmethyl-2-[2-methoxy-3,5-dichlorophenoxyethyl]pyrrolidine fumarate with a melting point of 162°–163° C. T.L.C. analysis does not reveal hexamethylene imino derivative.

EXAMPLE XIII

1-[1-cyclohexenylmethyl]-2-[2-(2-methoxy-3,5-dichlorophenoxy)ethyl]pyrrolidine

1-[1-cyclohexenylmethyl]-4-[2-methoxy-3,5-dichlorophenoxy]azepine (1) 2-[1-(1-cyclohexenylmethyl)-2-pyrrolidinyl]ethanol.

16.4 g of 2-[2-pyrrolidinyl]ethanol (0.143 mole) and 84.3 ml of 1.78 N alcoholic potassium hydroxide (0.150 mole) are introduced into a 500 ml balloon flask provided with a stirrer, a thermometer, a condenser and a dropping funnel, then 28 g of 1-bromomethylcyclohexene (90% purity) is dropped in.

The temperature rises from 20° to 55° C. and a precipitate is formed. After one hour of reaction the salts are filtered off and the filtrate is evaporated to dryness.

The residual oil is treated with 150 ml of water, then with hydrochloric acid until pH=1.

After two extractions with 100 ml of ethyl ether at a time, the aqueous phase is made alkaline with soda then extracted three times with 100 ml of ether. Those extracts are dried on magnesium sulfate, filtered and evaporated to dryness.

The residual oil is distilled under vacuum. 20.7 g of compound is obtained (B.P. under 2 mm of Hg: 100°–107° C.—$nD^{20}$=1.506).

(2) 2-[1-(1-cyclohexenylmethyl)-2-pyrrolidinyl]chloroethane.

17.8 g of 2-[1-(1-cyclohexenylmethyl) 2-pyrrolidinyl]ethanol (0.085 mole) and 50 ml of chloroform are introduced into a 250 ml balloon flask provided with a stirrer, a thermometer, a condenser and a dropping funnel, then 15.3 ml of thionyl chloride is dropped in, the temperature being kept at about 25°–25° C. by cooling.

The mixture is then heated under reflux for three hours.

The solution is evaporated to dryness, then the residue is treated with 20 ml of toluene. After evaporation to dryness under vacuum, the residue is suspended in 100 ml of ethyl acetate. The crystals are filtered and dried in a drying oven at 50° C.

19.4 g of compound is obtained (M.P.=122° C.).

(3) 1-[1-cyclohexenylmethyl] 2-[2-(2-methoxy-3,5-dichlorophenoxy)ethyl]pyrrolidine.

1-[1-cyclohexenylmethyl]-4-[2-methoxy -3,5-dichlorophenoxy]azepine.

60 ml of ethanol is introduced into a 250 ml balloon flask provided with a stirrer, a thermometer, a condenser and a dropping funnel, then 1.4 g of sodium is added gradually.

After total dissolution, 11.6 g of 3,5-dichloro guaiacol is added, then the solvent is evaporated under vacuum.

The solid residue is dissolved in 60 ml of DMF.

The solution is heated to about 100° C., then a solution of 8 g of 2-[1-(1-cyclohexenylmethyl)-2-pyrrolidinyl]chloroethane (0.030 mole) in 40 ml of DMF is dropped in.

Heating is kept for two hours then the solvent is evaporated to dryness under vacuum.

The residue is treated with 300 ml of water, then the mixture is made alkaline with ammonia. The suspension is extracted three times with 100 ml of ether and the organic phase is washed with 100 ml of water. The ethereal solution is dried on magnesium sulfate, then the solvent is evaporated to dryness under vacuum. 12 g of product is obtained.

The NMR spectrum corresponds to that of a mixture containing about 30% of pyrrolidine derivative and 70% of its azepine isomer.

The mixture is dissolved into 40 ml of methyl ethyl ketone and acidified at pH=1 with a concentrated solution of hydrochloric acid in isopropanol. Crystallization is started with seeding, then the mixture is left overnight.

The crystals are filtered, washed with isopropanol and dried in a drying oven at 60° C. 7.3 g of a product melting at about 172° C. is obtained. The NMR spectrum corresponds to that of a mixture containing 80 to 85% of azepine derivative.

The filtrate is evaporated to dryness. Then the residue is treated with 65 ml of isopropanol. The insoluble crystals are filtered, washed with isopropanol then dried in a drying oven at 50° C.

1 g of a product melting at about 160° C. is obtained, the NMR spectrum of which corresponds to that of 1-[1-cyclohexenylmethyl] 2-[2-(2-methoxy-3,5-dichlorophenoxy)ethyl]pyrrolidine.

The products according to the invention are used in the form of an injectable solution, collyrium or lotion the preparation of which is known per se.

The compounds of the invention can be used for local injection in the form of ampules with a dosage of 10 mg/5 ml. It is also possible for the compounds of the invention to be applied locally in the form of paint compositions.

The following examples concerning pharmaceutical preparations which are produced in conventional manner from the compounds of the invention.

EXAMPLE A
Injectable solution

| | |
|---|---|
| 1-Ethyl-2-[2-methoxy-3,5-dichlorophenoxyethyl] pyrrolidine hydrochloride | 10 mg |
| Potassium chloride | 44 mg |
| Water for injectable preparations q.s. | 2 ml |

EXAMPLE B
Collyrium

| | |
|---|---|
| 1-Methyl-2-[2-methoxy 3,5-dichlorophenoxy ethyl] pyrrolidine citrate | 1.60 g |
| Methyl parahydroxybenzoate | 1.30 g |
| Propylparahydroxybenzoate | 0.20 g |
| Water for injectable preparations q.s. | 1000 ml |

EXAMPLE C
Lotion

| | |
|---|---|
| 1-Ethyl-2-[2-methoxy 3,5-dichlorophenoxyethyl] pyrrolidine hydrochloride | 0.334 g |
| 95° Ethyl alcohol | 52 g |
| Water for injectable preparations q.s. | 100 ml |

The compounds of the invention have interesting pharmacological properties in regard to the central nervous system, in particular as local anaesthetics.

The toxicity of the compounds of the invention was determined in mice parenterally (intravenously, intraperitoneally and subcutaneously) and orally. Lethal doses 50 are shown by way of example in Table 1. In Table 1 and in the following tables, the compounds of the invention are numbered as indicated below:

| COMPOUNDS | NUMBERS |
|---|---|
| 1-Methyl-2-[2-methoxy-3,5-dichlorophenoxyethyl] pyrrolidine fumarate (racemic) | Compound 1 |
| 1-Methyl-2-[2-methoxy-3,5-dichlorophenoxyethyl] pyrrolidine (dextrorotatory) | Compound 2 |
| 1-Methyl-2-[2-methoxy-3,5-dichlorophenoxyethyl] pyrrolidine (levorotatory) | Compound 3 |
| 1-Ethyl-2-[2-methoxy-3,5-dichlorophenoxyethyl] pyrrolidine hydrochloride (racemic) | Compound 4 |
| 1-Ethyl-2-[2-methoxy-3,5-dichlorophenoxyethyl] pyrrolidine hydrochloride (dextrorotatory) | Compound 5 |
| 1-Ethyl-2-[2-methoxy-3,5-dichlorophenoxyethyl] pyrrolidine hydrochloride (levorotatory) | Compound 6 |
| 1-Allyl-2-[2-methoxy-3,5-dichlorophenoxyethyl] pyrrolidine fumarate (racemic) | Compound 7 |
| 1-Ethyl-2-[2-ethoxy-3,5-dichlorophenoxyethyl] pyrrolidine citrate (racemic) | Compound 8 |
| 1-Ethyl-2-[3,5-dichlorophenoxyethyl] pyrrolidine (racemic) | Compound 9 |
| 1-Methyl-2-[2-methoxy-3,5-dibromophenoxyethyl] pyrrolidine fumarate (racemic) | Compound 10 |
| 1-Methyl-4-[2-methoxy-3,5-dichlorophenoxy] hexamethylene imine hydrochloride | Compound 11 |
| 1-Allyl-4-[2-methoxy-3,5-dichlorophenoxy] hexamethylene imine citrate | Compound 12 |
| 1-Cyclohexyl 4-[2-methoxy 3,5-dichlorophenoxy] hexamethylene imine hydrochloride | Compound 13 |
| 1-Cyclohexyl 2-[2-methoxy-3,5-dichlorophenoxyethyl]pyrrolidine bis-phosphate | Compound 14 |
| 1-Cyclopropylmethyl 4-[2-methoxy 3,5-dichlorophenoxy]hexamethylene imine citrate | Compound 15 |
| 1-Cyclopropylmethyl 2-[2-methoxy 3,5-dichlorophenoxyethyl]pyrrolidine fumarate | Compound 16 |

TABLE 1
TOXICITY
DL 50 - MOUSE - mg/kg (base)

| COMPOUNDS | IV | IP | SC | PO |
|---|---|---|---|---|
| 1 | 34.7–36.5 | 160–192 | 597–651 | 521–561 |
| 2 | 27.5–28.2 | 161–168 | 702–800 | 543–561 |
| 3 | 44.9–45.2 | 182–192 | 543 | 434–486 |
| 4 | 35–32.3 | 137–141 | 365–377 | 574–597 |
| 5 | 29.6–30.9 | 149–156 | 464–487 | 565–574 |
| 6 | 32.7–35.5 | 151–157 | 377–381 | 484–518 |
| 7 | 28.9–32.2 | 186–189 | 777–821 | 479–518 |
| 8 | 25.3–25.7 | 152–160 | 469–488 | 684–689 |
| 9 | 36.4–37.3 | 117–119 | 248–257 | 244–253 |
| 10 | 43.2–45.7 | 149–154 | 382–431 | 340–371 |
| 11 | 34.3–36.3 | 168–169 | 248–271 | 643–679 |
| 12 | 31.6–36 | 182–195 | 60% mortality at 1400 mg/kg | 480–531 |
| 13 | 15.3–14.8 | 91.1–86.5 | 10% mortality at 180 mg/kg | 455–464 |
| 14 | 19.7–19.3 | 88.4–88 | 550–591 | 206–216 |
| 15 | 18.5–19.1 | 122–116 | 411–404 | 270–254 |
| 16 | 22.9–26.9 | 142–136 | 479–512 | 293–303 |

The local anaesthetic properties of the compounds of the invention were demonstrated from the different tests described hereinafter.

Local surface anaesthesia was determined by the Regnier method described in the "These Doc Med Paris 1929". This method comprises studying the suppression of the oculopalpebral reflex on the cornea of a rabbit.

Taking a batch of ten rabbits, the depth of cornean anaesthesia after instillation in the eye of the two drops of the aqueous solution of the product to be studied is measured by comparison with the depth of cornean anaesthesia produced by aqueous solutions of cocaine hydrochloride at different concentration levels. The experiment is carried out in a crossed test mode. The average number per hour of strokes with a hair on the cornea, which do not produce any reaction, indicates the intensity of anaesthesia. It is therefore possible to evaluate the percentage of anaesthesia in dependence on concentration and graphically determine the CE 50.

The term CE 50 is used to denote the concentration of a solution which, injected, in a given volume, abolishes the sensitive response in 50% of the animals.

The activity indices which are defined by:

TABLE II $$\text{THE RATIO} = \frac{\text{CE 50 of the reference anaesthetic}}{\text{CE 50 of the product to be studied}}$$

INDEX OF ACTIVITY
SURFACE ANAESTHESIA IN RABBITS

| COMPOUNDS | 1 | 2 | 3 | 4 | 5 | 6 | 7 | 11 | 16 |
|---|---|---|---|---|---|---|---|---|---|
| Activity | 1.36 | 1.72 | 1.92 | 4.65 | 3.52 | 2.12 | 1.84 | 1.56 | 5.68 |

TABLE II-continued $$\text{THE RATIO} = \frac{\text{CE 50 of the reference anaesthetic}}{\text{CE 50 of the product to be studied}}$$

INDEX OF ACTIVITY
SURFACE ANAESTHESIA IN RABBITS

| COMPOUNDS | 1 | 2 | 3 | 4 | 5 | 6 | 7 | 11 | 16 |
|---|---|---|---|---|---|---|---|---|---|
| index | | | | | | | | | |

Anaesthetic conduction activity was carried out in the following manner:

A local anaesthetic injected in depth into the upper leg of a rat along the path of the sciatic nerve, at a rate of 1 ml, causes anaesthesia of the nervous terminations which is characterised and measured by pinching the middle toes of the foot of the rear leg of the rat.

The compounds of the invention or the reference anaesthetic (xylocaine) are injected, in a volume of 1 ml, for a given concentration, in a batch of ten male rates.

At 30 minutes, 1 hour, 2 hours and 3 hours after administration, the three middle toes of the rear leg are pinched at the positive responses of the animal to each toe-pinching action are noted.

Summing the positive reactions of the ten animals makes it possible to obtain the percentage of anaesthesia. The CE 50 is then determined by graph means.

The activity indices are set out in Table III.

TABLE III

ACTIVITY INDEX OF CONDUCTION ANAESTHESIA IN RATS

| | COMPOUNDS | | | | | | | |
|---|---|---|---|---|---|---|---|---|
| | 1 | 2 | 3 | 4 | 5 | 6 | 8 | 11 | 12 |
| Activity index | 3.31 | 4 | 2.1 | 2.4 | 4.14 | 3.4 | 2.44 | 2.4 | 2.8 |

Infiltration anaesthesia was studied in guinea pigs in accordance with the method described in Bulbring and Wajda in J. Pharmacol. Exp. Ther. (1945) 85 78–84.

This method is based on the disappearance of cutaneous reflex caused in the guinea pig by a mechanical stimulus.

We worked on batches of ten male adult guinea pigs and, the day before, carefully removed the hair from the back of the guinea pigs over a surface area of 16 cm$^2$. Ink was used to define four regions ABCD such that: A=left front region; B=right front region; C=left rear region; D=right rear region.

At the center of each region, a check was made for the appearance of the cutaneous reflex in response to a single excitation caused by a pin. 0.2 ml of the solution of anaesthetic in the injectable isotonic solute of sodium chloride is then injected. Five minutes afterwards, the center of the intradermic pimple produced is regularly excited at the rate of 1 excitation every three seconds until the reflex appears or, if anaesthesia is total, a number of times equal to 6. Exploration of the anesthetic action is continued every 5 minutes for a period of 30 minutes.

The reference substances is procaine.

Taking a batch of 10 guinea pigs, for a given concentration of procaine and compound according to the invention, 5 animals are tested in regions A and C with the compound of the invention and the remainder are tested with procaine in regions B and D. The next day, a crossed test is carried out, by reversing the injection regions.

Taking two other batches, the same experiment is repeated with two other levels of concentration in respect of the compound of the invention and procaine, and the average of excitation effects obtained on 10 guinea pigs is calculated in respect of each level of concentration.

The percentage of anaesthesia in dependence on concentration makes it possible for us to determine the CE 50 by graph means.

The activity indices are set out in Table IV.

TABLE IV

ACTIVITY INDEX OF
INFILTRATION ANAESTHESIA IN GUINEA PIGS

| | COMPOUNDS | | | | | | | | |
|---|---|---|---|---|---|---|---|---|---|
| | 1 | 2 | 3 | 5 | 6 | 8 | 9 | 10 | 14 | 16 |
| Activity index | 3.58 | 3.1 | 4.2 | 1.65 | 2.69 | 5 | 1.8 | 3.17 | 4.07 | 2.55 |

The results of these tests prove anaesthetic activity of the compounds of the invention, which is 2 to 4 times greater on average than the activity of the reference anaesthetics (xylocaine, procaine and cocaine).

The interest aroused by the experiments carried out on laboratory animals has been very widely justified in human clinical tests in respect of the compounds of the invention. The following may be mentioned by way of example:

The case of a 68 year old patient suffering from postphlebitic illness with serious bilateral internal susmalleolar trophic disturbances.

These disturbances irritated old leg ulcers which are cicatrized at the present time but which are the origin of intense itching and nocturnal recrudescence with lichenification. Local application of 0.3% 1-ethyl-2-[2-methoxy-3,5-dichlorophenoxyethyl]pyrrolidine lotion causes relief from the itching, which relief becomes increasingly substantial and in particular increasingly prolonged after each application, to such an extent that the scratching lesions disappear, which causes the lichen to disappear.

A 38 year old patient had to undergo oesteosynthesis on the left tibia following a skiing accident. Orthopaedic healing is perfect and recovery is excellent. However, the patient is greatly disturbed by a "pruritus ferox", sine materia at the position of the scar.

The application of 0.3% 1-methyl-2-[2-methoxy-3,5-dichlorophenoxyethyl]pyrrolidine lotion causes considerable relief from the pruritus, as from the first day, and the pruritus completely disappears in a week.

A 67 year old patient has been suffering for a number of months from severe anal pruritus resulting in: anorexia and insomnia, resulting in suicidal tendencies.

All proctological and dermatological treatments have remained ineffective.

In 3 days, the continuous application of compresses soaked with 0.3% 1-ethyl-2-[2-ethoxy-3,5-dichlorophenoxyethyl]pyrrolidine lotion causes the pruritus to totally and definitely disappear: this improvement causes a considerable restoration of appetite to such an extent that the patient puts on weight to a hitherto unknown extent.

A young 17 year old man suffers from stage IV Hodgkin's disease, one of the indicating signs of which was intensive pruritus predominating on the front surface of the two forearms. In parallel with chemotherapeutic treatment, he was advised to brush on the solution of 1-methyl-2-[2-methoxy-3,5-dibromophenoxyethyl]pyrrolidine.

Although relief is incomplete it is satisfactory and enables the patient to sleep again.

In a 47 year old patient, the instillation of two drops of 1-ethyl-2-[3,5-dichlorophenoxyethyl]pyrrolidine solution permits a metal foreign body encrusted in the conjunctiva to be easily extracted.

What is claimed:

1. A compound of the formula

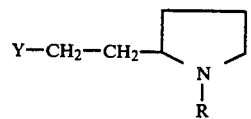

wherein Y is hydroxyl or chlorine and R is 1-cyclohexenylmethyl.

2. The compound of claim 1 wherein Y is chlorine.
3. The compound of claim 1 wherein Y is hydroxyl.

* * * * *